(12) United States Patent
Bonte et al.

(10) Patent No.: US 6,641,848 B1
(45) Date of Patent: Nov. 4, 2003

(54) SAPONIN OR SAPOGENOL COMPOSITIONS FOR INCREASING COLLAGEN IV SYNTHESIS

(75) Inventors: Frédéric Bonte, Orleans (FR); Marc Dumas, Orleans (FR); Pierre Perrier, Orleans (FR)

(73) Assignee: Parfums Christian Dior, Paris (FR)

( * ) Notice: Subject to any disclaimer, the term of this patent is extended or adjusted under 35 U.S.C. 154(b) by 0 days.

(21) Appl. No.: 09/700,654

(22) PCT Filed: May 28, 1999

(86) PCT No.: PCT/FR99/01260

§ 371 (c)(1),
(2), (4) Date: Nov. 17, 2000

(87) PCT Pub. No.: WO99/62480

PCT Pub. Date: Dec. 9, 1999

(30) Foreign Application Priority Data

May 29, 1998 (FR) .............................................. 98 06821

(51) Int. Cl.⁷ .............................. A61K 6/00; A61K 7/00; A61K 35/78; A01N 65/00; A01N 25/00
(52) U.S. Cl. ..................... 424/757; 424/401; 514/844
(58) Field of Search ............................... 424/450, 195.1, 424/401, 757; 514/844

(56) References Cited

U.S. PATENT DOCUMENTS

| | | | |
|---|---|---|---|
| 4,524,067 A | * 6/1985 | Arichi et al. ................... | 514/33 |
| 5,607,693 A | 3/1997 | Bonte et al. | |
| 5,609,873 A | * 3/1997 | Meybeck et al. ......... | 424/195.1 |
| 5,624,673 A | 4/1997 | Bonte et al. | |
| 5,663,160 A | 9/1997 | Meybeck et al. | |
| 5,723,149 A | * 3/1998 | Bonte et al. ................. | 424/450 |
| 5,747,538 A | 5/1998 | Meybeck et al. | |
| 5,770,223 A | 6/1998 | Bonte et al. | |
| 6,004,568 A | 12/1999 | Bonte et al. ................. | 424/401 |

FOREIGN PATENT DOCUMENTS

| | | |
|---|---|---|
| EP | 826 367 | 3/1998 |
| WO | WO 96/25143 | 8/1996 |
| WO | WO 97/28814 | 8/1997 |

OTHER PUBLICATIONS

Gomes Da Silva, W., "The Brazil Nut (*Bertholletia excelsa* H.B.K.—Family: Lecythidaceae); Note II: Lipids: Study of the Chemical Composition"; vol. 74, No. 7, 1997, pp. 311–314.

Chemical Abstracts, vol. 128, No. 4, Jan. 26, 1998 Columbus, Ohio, US; Abstract No. 32365, El–Shamy, Ali M. et al. "Phytochemical Study of Clerodendron Inerme L. Growing in Egypt".

Chemical Abstracts, vol. 116, No. 5, Feb. 3, 1992, Columbus, Ohio; Abstract No. 37930; R. Zafar "Chemical examination of the leaves of *Diospyros montana* Roxb", vol. 28, No. 9, 1991, pp. 29–29.

A.Y. Leung "Encyclopedia of Common Natural Ingredients Used in Food, Drugs, and Cosmetics" 1996; pp. 284, col. 1, paragraph 3; pp. 28; col. 2; paragraph 3; pp. 285, col. 1, line 2.

* cited by examiner

Primary Examiner—Theodore J. Griares
Assistant Examiner—Lauren Q. Wells
(74) Attorney, Agent, or Firm—Smith, Gambrell & Russell LLP

(57) ABSTRACT

The present invention relates in general terms to the use of saponins or sapogenols, particularly those extracted from a plant, preferably from soya or Medicago, in cosmetology and for the manufacture of pharmaceutical compositions for treating the skin in order to increase the amount of collagen IV in the dermo-epidermal junction. It further relates to novel cosmetic or pharmaceutical compositions which promote an increase in the amount of collagen IV in the dermo-epidermal junction, and to a method of cosmetic treatment using a saponin or a sapogenol. The invention is applicable in cosmetics, preferably in an anti-wrinkle treatment, and in pharmacy in the treatment of diseases associated with a deficiency of the dermo-epidermal junction resulting from an insufficient amount of collagen IV.

17 Claims, No Drawings

SAPONIN OR SAPOGENOL COMPOSITIONS FOR INCREASING COLLAGEN IV SYNTHESIS

This Application is a 371 of PCT/FR99/01260 filed May 28, 1999, which claims priority to French Application 98/06821 filed May 29, 1998.

The present invention relates in general terms to the use of saponins or sapogenols in cosmetology and for the manufacture of pharmaceutical compositions for treating the skin in order to increase the amount of collagen IV in the dermo-epidermal junction.

It further relates to novel cosmetic or pharmaceutical compositions which promote an increase in the amount of collagen IV in the dermo-epidermal junction, and to a method of cosmetic treatment using a saponin or a sapogenol.

The dermo-epidermal junction is known to be a complex structure which assures the cohesion and exchanges between the dermis and the epidermis which are essential for the skin to function properly.

It is further known that type IV collagen, also called collagen IV, is a major constituent of the dermo-epidermal junction, which is involved especially in maintaining a functional interface between the dermis and the epidermis.

The optimum physiological state of the dermo-epidermal junction depends on there being a sufficient amount of collagen IV in this dermo-epidermal junction.

Therefore, to maintain or restore the physiological state of the dermo-epidermal junction, it is desirable to have a means of increasing the amount of collagen IV therein.

It has been discovered that triterpenic saponins and sapogenols, preferably of type A or type B and especially those which are cosmetically or pharmaceutically acceptable, are particularly appropriate as agents for increasing the amount of collagen IV in the dermo-epidermal junction; it is this discovery which constitutes the basis of the present invention.

Thus, according to a first feature, the present patent application aims to cover the use of at least one cosmetically acceptable saponin or sapogenol of triterpenic character, particularly a saponin or sapogenol extracted from a plant, preferably from soya or a plant of the Medicago type, or of a plant extract rich in such compounds, as a cosmetic agent for increasing the amount of collagen IV in the dermo-epidermal junction.

As well as the cosmetic field, the invention is also applicable in the pharmaceutical field, especially the dermatological field.

Thus, according to a second feature, the present patent application aims to cover the use of at least one pharmaceutically acceptable saponin or sapogenol of triterpenic character, particularly a saponin or sapogenol extracted from a plant, preferably from soya or a plant of the Medicago type, or of a plant extract rich in such compounds, for the manufacture of a pharmaceutical composition, especially dermatological composition, for treating pathological conditions associated with a deficiency of the dermo-epidermal junction resulting from an insufficient amount of collagen IV.

A very large number of saponins and sapogenols of triterpenic character are found to be appropriate within the framework of the use according to the present invention, in the cosmetic or pharmaceutical field.

These compounds, which will have to be cosmetically or pharmaceutically acceptable within the framework of a cosmetic or pharmaceutical use, will advantageously be extracted from plants. They could also be obtained by chemical synthesis, as is easily comprehensible and known to those skilled in the art.

In particular, it will be possible to use saponins extracted from plants, preferably those extracted from *Glycine max* (soya), *Phaseolus vulgaris, Phaseolus aureus, Phaseolus lunatus, Vicia faba, Lens culinaris, Cicer arietum, Vigna angularis, Vigna mungo, Oxytropis ochrocephala, Oxytropis glabra, Pisum sativum, Sophora favescens, Asparalus membranaceus, Crotalaria albida, Arachis hypogea, Galega officinalis, Wistaria brachybotrys* and *Trifolium repens*, or those extracted from plants of the Medicago type, particularly *Medicago alfalfa* and *Medicago sativa*, which is often called "alfalfa".

According to a third feature, the present patent application aims to cover the use of at least one saponin or sapogenol extracted from a plant rich in such compounds and selected from *Glycine max* (soya), *Phaseolus vulgaris, Phaseolus aureus, Phaseolus lunatus, Vicia faba, Lens culinaris, Cicer arietum, Vigna angularis, Vigna mungo, Oxytropis ochrocephala, Oxytropis glabra, Pisum sativum, Sophora favescens, Asparalus membranaceus, Crotalaria albida, Arachis hypogea, Galega officinalis, Wistaria brachybotrys* and *Trifolium repens*, or a plant of the Medicago type, particularly *Medicago alfalfa* and *Medicago sativa*, or "alfalfa", as a cosmetic agent for increasing the amount of collagen IV in the dermo-epidermal junction.

According to a fourth feature, the present invention aims to cover the use of at least one saponin or sapogenol extracted from a plant rich in such compounds and selected from *Glycine max* (soya), *Phaseolus vulgaris, Phaseolus aureus, Phaseolus lunatus, Vicia faba, Lens culinaris, Cicer arietum, Vigna angularis, Vigna mungo, Oxytropis ochrocephala, Oxytropis glabra, Pisum sativum, Sophora favescens, Asparalus membranaceus, Crotalaria albida, Arachis hypogea, Galega officinalis, Wistaria brachybotrys* and *Trifolium repens*, or a plant of the Medicago type, particularly *Medicago alfalfa* and *Medicago sativa*, or "alfalfa", for the manufacture of a pharmaceutical composition, especially dermatological composition, for treating pathological conditions associated with a deficiency of the dermo-epidermal junction resulting from an insufficient amount of collagen IV.

Soya and plants of the Medicago type, such as *Medicago sativa*, are particularly appropriate plants for providing saponins or sapogenols which can be used within the framework of the invention, since said compounds are of the triterpenic type and, in particular, of type A or type B.

These saponins or sapogenols of triterpenic character will advantageously comprise type A or type B triterpenic soya saponins or soya sapogenols and may be extracted in particular from a plant of the Medicago type, such as *Medicago alfalfa* and *Medicago sativa*.

These type A or type B triterpenic soya saponins or soya sapogenols are well known in the literature (cf. on the one hand the article by Georges Massiot, Catherine Lavaud, Dominique Guillaume and Louisette Le Men-Olivier in J. Agric. Food Chem. (1988), 36, pages 902–909, and on the other hand the book entitled "Saponins" by Hostettman K. and Marston A. (1995), published by Cambridge University Press, particularly Appendix 2, references 446 to 460 and 517 to 519. They have the following chemical formulae:

type A soya sapogenol

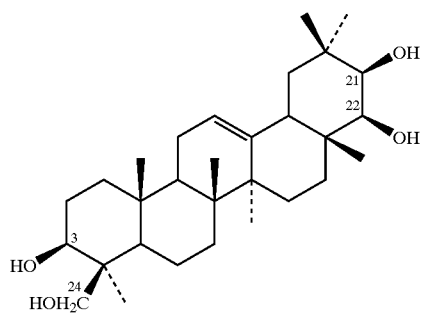

type B soya sapogenol

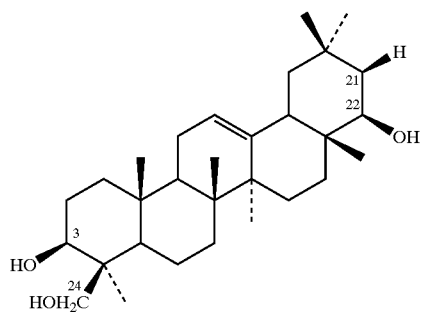

Sapogenols do not contain a sugar substituent, so they are generally called aglycones. On the other hand, they can be substituted by sugars or sugar chains and are then called soya saponins, which can thus be of type A or type B.

The following may be mentioned as examples:

Soya sapogenol A. aglycone
(according to Appendix 2 of Hostettman and Marston
(1995) - Cambridge University Press)

| Name | Structure | Plant extracted | Bibliographic reference |
|---|---|---|---|
| No. 517 Soya saponin $A_2$ | 3-GlcA$^2$-Gal 22-Ara$^3$-Glc | Glycine max (Leguminosae) | Kitagawa et al. 1985c |
| No. 518 Soya saponin $A_1$ | 3-GlcA$^2$-Gal$^2$-Glc 22-Ara$^3$-Glc | Glycine max (Leguminosae) | Kitagawa et al. 1985a |
| No. 519 Soya saponin $A_3$ | 3-GlcA$^2$-Gal$^2$-Rha | Glycine max (Leguminosae) | Curl et al. 1988b |

Soya sapogenol B. aglycone
(according to Appendix 2 of Hostettman and Marston
(1995) - Cambridge University Press)

| Name | Structure | Plant extracted | Bibliographic reference |
|---|---|---|---|
| No. 446 | 24-Glc | Phaseolus vulgaris (Leguminosae) | Jain et al. 1988 |
| No. 447 Soya saponin IV | 3-GlcA$^2$-Ara | Glycine max (Leguminosae) | Burrows et al. 1987 |
| No. 448 Soya saponin III | 3-GlcA$^2$-Gal | G. max (Leguminosae) | Kitagawa et al. 1982 |
| No. 449 Azuki saponin II | 3-GlcA$^2$-Glc | Vigna angularis (Leguminosae) Medicago sativa (Leguminosae) | Kitagawa et al. 1983c Kitagawa et al. 1988d |
| No. 450 Phaseoluside A | 3-Glc$^4$-Glc ½3 Glc | Phaseolus vulgaris (Leguminosae) | Jain et al. 1991 |
| No. 451 Soya saponin II | 3-GlcA$^2$-Ara$^2$-Rha | Glycine max (Leguminosae) | Kitagawa et al. 1982 |
| No. 452 | 3-GlcA$^2$-Ara$^2$-Rha | Oxytropis ochrocephala (Leguminosae) O. glabra (Leguminosae) | Sun et al. 1987 Sun et al. 1991 |
| No. 453 Soya saponin V | 3-GlcA$^2$-Gal$^2$-Glc | Glycine max (Leguminosae) Phaseolus vulgaris (Leguminosae) | Taniyama et al. 1988b Curl et al. 1988a |
| No. 454 Soya saponin I | 3-GlcA$^2$-Gal$^2$-Rha | Glycine max (Leguminosae) Medicago sativa (Leguminosae) Pisum sativum (Leguminosae) | Kitagawa et al. 1976b Kitagawa et al. 1988d Price and Fenwick 1984 |
| No. 456 Azuki saponin V | 3-GlcA$^2$-Glc$^2$-Rha | Vigna angularis (Leguminosae) Medicago sativa (Leguminosae) | Kitagawa et al. 1983d Kitagawa et al. 1988d |
| No. 457 | 3-GlcA$^4$-Glc$^2$-Rha | Oxytropis ochrocephala (Leguminosae) | Sun et al. 1987 |
| No. 458 Astragaloside VIII | 3-GlcA$^2$-Xyl$^2$-Rha | Astragalus membranaceus (Leguminosae) | Kitagawa et al. 1983e |
| No. 459 | 3-GlcA$^4$-Glc$^2$-Rha ½2 Glc | Oxytropis glabra (Leguminosae) | Sun and Jia 1990 |
| No. 460 | 3-GlcA$^2$-Gal$^2$-Rha ½6 Glc | Crotalaria albida (Leguminosae) | Ding et al. 1991a |

The above-mentioned triterpenic saponins or sapogenols can be extracted from any part of the plant, but will preferably be extracted from the roots in the case of Medicago and from the seeds in the case of soya.

The extraction conditions are well known to those skilled in the art, who may refer e.g. to the document WO 92/09262, which is incorporated here by way of reference.

Within the framework of the use according to the present invention, the proportion of saponin(s) or sapogenol(s), or of plant extract containing them, is advantageously between 0.001% and 5% by weight, preferably between 0.01 and 2% by weight, based on the total weight of the final cosmetic or pharmaceutical composition.

It has also been discovered, totally unexpectedly, that the beneficial effect of saponins and sapogenols, irrespective of their character, i.e. even if said saponin or said sapogenol is not of triterpenic character, although it is preferable to use a saponin or sapogenol of triterpenic character, preferably of type A or type B, can be substantially increased if these compounds are used in association with an ecdysteroid or an acetylated ecdysteroid derivative such as, in particular, β-ecdysone or ecdysterone.

Ecdysteroids, and particularly ecdysterone, are well-known natural substances found especially in insects and in certain plants such as Polypodium vulgare and Cyanotis arachnoidea.

Within the framework of the use of a saponin or sapogenol in association with an ecdysteroid, these compounds will be used in a weight ratio preferably of between 1:10 and 10:1 and particularly preferably of 1:1.

The saponins or sapogenols can also be used in association with another active substance selected e.g. from the group consisting of madecassic acid, asiatic acid, madecassoside, asiaticoside, α-1-proteinase inhibitor, collagenase inhibitors such as retinoic acid, elastase inhibitors, lysine, proline, 2-oxoglutarate, ginsenoside $R_0$, vitamin D and derivatives thereof, other vitamins, particularly vitamin A, B or E, xanthines, tyrosine or derivatives thereof, for example glucose tyrosinate or malyltyrosine, quinine or derivatives thereof, rubefacients such as methyl nicotinate, keratin hydrolyzates, trace elements such as zinc, selenium or copper, 5-α-reductase inhibitors such as progesterone or cyproterone acetate, minoxidil, azelaic acid and derivatives thereof, 1,4-methyl-4-azasteroid, particularly 17β-N,N-diethylcarbamoyl-4-methyl-4-aza-5-α-androstan-3-one, or an extract of *Serenoa repens*.

In this case the concentration of this (these) other active substance(s) is between 0.0001% and 5% by weight, based on the weight of the final composition.

These substances, including the saponins or sapogenols, can optionally be at least partially incorporated into hydrated lipidic lamellar phases or liposome-type vesicles.

According to a fifth feature, the present patent application aims to cover novel cosmetic or pharmaceutical compositions which promote an increase in the amount of collagen IV in the dermo-epidermal junction.

These compositions are essentially characterized in that they contain an effective amount of at least one saponin or sapogenol, irrespective of its character, can be of non-triterpenic character, but preferably at least one saponin or sapogenol of triterpenic character, particularly preferably of type A or type B, in association with at least one ecdysteroid, particularly β-ecdysone or ecdysterone.

In this case the above-mentioned saponin or sapogenol and the above-mentioned ecdysteroid are associated in a weight ratio of between 1:10 and 10:1 and preferably of 1:1.

According to a sixth feature, the present patent application aims to cover a method of cosmetic treatment in which an effective amount of at least one saponin or at least one sapogenol as defined above, optionally in association with one or more other active substances such as those mentioned above, and/or in association with an ecdysteroid, particularly ecdysterone, is administered topically to a person in need thereof.

Other objects, characteristics and advantages of the invention will become clearly apparent from the following explanatory description referring to several Examples, which are given by way of illustration and cannot therefore in any way limit the scope of the invention.

In the Examples, the percentages are expressed by weight, the temperature is room temperature and the pressure is atmospheric pressure, unless indicated otherwise. In the case of the extracts, their amounts are expressed by dry weight.

EXAMPLE 1

Demonstration of the Increase in the Amount of Collagen IV Due to Saponins Extracted From Soya Seeds A soya seed extract commercially available under the reference SOY SELECT LOT 26040/2 from the Italian company Indena is used in this Example.

According to the marketing information, this extract contains saponins of the "soya saponin" category in a proportion of 29 to 30% by dry weight, with a predominance of group B soya sapogenols.

To validate the pertinence of the chosen experimental protocol, a series of these tests was carried out with a positive control, namely transforming growth factor beta (TGF-beta), which is known to increase the amount of collagen IV in a culture of human keratinocytes. Reference may be made to the article by Köning A. and Bruckner-Tuderman L., J. Cell. Biol., May 1992, 117(3), 679–85.

1. Test Protocol a. Origin of the Keratinocytes:

The cultures of normal human keratinocytes (NHK) are grown from a surgical specimen of healthy skin. In the present study, the tests were carried out on a strain of cells, denoted by HK 44, originating from a facelift performed on a 44-year-old caucasian woman.

b. Culture Conditions:

The keratinocytes are cultured in K-SFM growth medium, which is a complete specific keratinocyte culture medium (SFM=serum free medium) complemented with EGF (epidermal growth factor) and pituitary extract, said medium being marketed by Gibco, France. The cells were subcultured once from the primary culture in one passage, denoted by P1.

c. Treatment Conditions:

The cells are inoculated in 96-well culture plates at a rate of 25,000 NHK per well in K-SFM. After 24 h of incubation, which is necessary for good adhesion of the cells, the inoculation medium is withdrawn and replaced with K-SFM diluted 50-fold in the same base medium, but devoid of EGF and pituitary extract.

The product to be tested according to the invention, dissolved in DMSO at the various concentrations reported in Table I below, is then added and the mixture is cultured for 72 h.

The controls will receive the same amount of DMSO solvent as for the product tested at a final concentration of 0.1%.

The culture supernatants are recovered for carrying out an ELISA, as explained below.

d. ELISA of the Collagen IV:

The protocol for assaying the collagen IV by an ELISA method is adapted from that described by DUMAS M. et al. in Mechanisms of Ageing and Development, 1994, 73, pages 179–187.

An anti-human collagen IV antibody, supplied by Institut Pasteur, Lyon, France, is used. A calibration curve is plotted using human placental collagen IV from Sigma. In parallel, an overall assay of the proteins is performed by the bicinchoninic acid technique, using the BCA kit marketed by Sigma, France, in order to relate the amount of collagen IV to the proportion of cellular proteins.

Six cultures are prepared for each of the three concentrations and for the control test.

e. Expression of the Results and Statistical Interpretation:

The results of increasing the amount of collagen IV in a keratinocyte culture are expressed in nanograms of collagen IV per 100 μg of proteins after culture for 72 h.

The activity A of the product is expressed as a percentage and corresponds to the following formula:

$$A = \left(\frac{Q_s - Q_t}{Q_t}\right) \times 100$$

where:

Qs is the amount of collagen IV in the treated NHK, expressed in ng per 100 μg of proteins, after 72 hours;

Qt is the amount of collagen IV in the DMSO control NHK, expressed in ng per 100 µg of proteins, after 72 hours.

The results obtained on the treated cultures (n=6) and control cultures (n=6) are compared by the unpaired Student t-test, the significance level being p=0.05.

2. Results and Conclusion

The results are reported in Table I below on the basis of the mean of the measurements on the different cultures:

TABLE I

| PRODUCT | Q (ng collagen IV/100 µg proteins; at 72 h) | A (%) | Significance p = 0.05 |
|---|---|---|---|
| DMSO control | 3.743 ± 0.443 | 0 | |
| positive control (TGF-beta) 10 ng/ml | 5.615 ± 0.595 | +50 | S |
| soya saponins 2.5 µg/ml | 3.931 ± 0.426 | +5 | NS |
| soya saponins 5 µg/ml | 4.474 ± 0.511 | +19 | S |
| soya saponins 10 µg/ml | 4.762 ± 0.591 | +27 | S |
| soya saponins 25 µg/ml | 5.152 ± 0.596 | +37.5 | S |

S = significant
NS = not significant

It will be noted that the proportion of collagen IV is expressed in nanograms per 100 µg of proteins after 72 h of contact with the cells.

It is clearly apparent that the saponins tested significantly increase the amount of collagen IV in a human keratinocyte culture.

It will also be noted that the positive control (TGF-beta) responds significantly to the chosen experimental protocol, confirming its validation and the pertinence of the tests performed.

Thus saponins, particularly those extracted from soya, can be used in cosmetics or in pharmacy or dermopharmacy for increasing the amount of collagen IV. In this case they make it possible to strengthen the structure and properties of the dermo-epidermal junction, which is an exchange zone between the dermis and the epidermis constituting very important zones for keratinocyte differentiation processes.

EXAMPLE 2

Demonstration of the Increase in the Amount of Collagen IV in the Presence of Medicago Saponins This test is performed as follows:

The test product, consisting of saponins from *Medicago sativa* roots, is commercially available and marketed by Berkem in powder form.

The tests were performed blind, the product being called *Medicago saponin*.

1. Test Protocol a. Origin of the Keratinocytes:

The cultures of normal human keratinocytes (NHK) are grown from a surgical specimen of healthy skin. In the present study, the tests were carried out on a strain of cells, denoted by NHK 555, originating from a facelift performed on a 48-year-old caucasian woman.

b. Culture Conditions:

The keratinocytes are cultured in the same way as that described in the previous Example, except that the cells were subcultured 4 times and harvested at the stage of the 4th subculture or 4th passage, denoted by P4.

c. Treatment Conditions:

The cells are inoculated in 96-well culture plates at a rate of 30,000 NHK per well in K-SFM.

After 24 h of incubation, which is necessary for good adhesion of the cells, the medium is replaced with a K-SFM diluted to 2%, limiting the proliferation of the keratinocytes.

Immediately before use, the products according to the invention are prepared in DMSO in respective proportions of 2.5, 10 and 25 mg/ml from the commercially available product, and these stock solutions are introduced into the study medium at a final concentration of 0.1% V/V, i.e. test concentrations of 2.5, and 25 µg/ml. The control receives the excipient for the products, i.e. 0.1% V/V of DMSO.

The absence of cytotoxicity of the product according to the invention at the different test concentrations was also demonstrated with the aid of XTT viability tests from BOEHRINGER, France.

After 48 h of treatment, the incubation supernatants are withdrawn for assay of the collagen IV present. The BCA method from SIGMA is used to assay the proteins on the cellular tapetum remaining in the wells in order to relate the amount of collagen IV present to the proportion of cellular proteins.

d. ELISA of the Collagen IV:

The assay protocol is the same as that of Example 1, except that the following modifications were made in the development of the assay:

First antibody: anti-human collagen IV rabbit monoclonal antibody from INSTITUT PASTEUR DE LYON, ref. 20411.

Calibration range prepared with type IV human collagen of human placental origin, SIGMA, reference C5533.

e. Expression of the Results and Statistical Interpretation:

The results of the experiments, expressed by the method described in e) of Example 1, are given in Table II below.

2. Results and Conclusion

The results are given in Table II below on the basis of the mean of the measurements on the different cultures:

TABLE II

| PRODUCT | Q (ng collagen IV/100 µg proteins; at 48 h) | A (%) | Significance p = 0.05 |
|---|---|---|---|
| CONTROL: 2% K-SFM + 0.1% DMSO | 1.565 ± 0.314 | 0 | |
| alfalfa saponins (2.5 µg/ml) | 1.745 ± 0.409 | +11 | NS |
| alfalfa saponins (10 µg/ml) | 2.858 ± 0.529 | +83 | S |
| alfalfa saponins (25 µg/ml) | 2.336 ± 0.523 | +49 | S |

S = significant
NS = not significant

A significant increase is found in the amount of collagen TV present in normal human keratinocyte cultures prepared in the presence of saponins from *Medicago sativa* or alfalfa roots. The active concentrations of saponins are 10 and 25 µg/ml, the maximum activity being at 10 µg/ml.

Thus the product according to the invention is active and can be used as a cosmetic agent for the manufacture of cosmetic, pharmaceutical or dermatological compositions for strengthening the dermo-epidermal cohesion as in Example 1.

EXAMPLE 3

Demonstration of the Increase in the Amount of Collagen IV in the Presence of Saponins Extracted from Soya Seeds and Beta-ecdysone The protocol is the same as that described in Example 1, except that the extract of soya seeds (reference SOY SELECT LOT 26040/2, available from the Italian company Indena) is used in association with beta-ecdysone, these two components being in a weight ratio of 1/1, and except that the contact time between the test products and the cells is 48 hours (instead of 72 hours).

The results are given in Table III below on the basis of the mean of the measurements on the different cultures:

TABLE III

| PRODUCT | Q (ng collagen IV/100 µg proteins; at 48 h) | A (%) | Significance p = 0.05 |
|---|---|---|---|
| DMSO control | 1.565 ± 0.314 | 0 | |
| soya saponins 2.5 µg/ml | 1.643 ± 0.320 | +5 | NS |
| soya saponins 2.5 µg/ml and beta-ecdysone 2.5 µg/ml | 2.441 ± 0.360 | +56 | S |
| soya saponins 5 µg/ml | 1.682 ± 0.317 | +7.5 | NS |
| soya saponins 5 µg/ml and beta-ecdysone 5 µg/ml | 2.081 ± 0.340 | +33 | S |
| soya saponins 10 µg/ml | 1.972 ± 0.331 | +26 | S |
| soya saponins 10 µg/ml and beta-ecdysone 10 µg/ml | 2.003 ± 0.336 | +28 | S |
| soya saponins 20 µg/ml | 1.975 ± 0.335 | +26 | S |
| soya saponins 20 µg/ml and beta-ecdysone 20 µg/ml | 1.998 ± 0.342 | +27.5 | S |

S = significant
NS = not significant

It is seen from Table III that the use of soya saponins in association, or combination, with beta-ecdysone at certain concentrations (2.5 and 5 µg/ml for each of the two components) is even more effective than the use of soya saponins alone for increasing the amount of collagen IV in a medium containing normal human keratinocytes.

The same experiment was conducted using beta-ecdysone alone. No increase in the amount of collagen IV was found.

The inventors have therefore concluded that there is a synergistic effect between soya saponins and beta-ecdysone as regards the capacity of these components to cause an increase in the amount of collagen IV in a medium containing normal human keratinocytes.

The combination of a soya saponin with beta-ecdysone therefore seems to be very effective as a means of increasing the amount of collagen IV in a medium containing normal human keratinocytes.

Thus the association of saponin and ecdysteroid according to the invention is of great value for cosmetic and pharmaceutical applications, especially dermatological applications.

EXAMPLE 4

| Cream for combating ageing lines | |
|---|---|
| Retinol | 4000 IU |
| Type B soya saponins | 0.01 g |
| Glycerol | 3 g |
| Extract of *Commiphora mukkul* | 0.1 g |
| Fluid emulsion excipient | qsp 100 g |

This fluid emulsion is to be used in the evening for treating wrinkles and is to be worked into the skin.

EXAMPLE 5

| Cream for combating wrinkles and preventing photo-ageing | |
|---|---|
| Retinol | 2000 IU |
| Retinol palmitate | 0.01 g |
| Ascorbyl palmitate | 0.1 g |
| Wheat proteins | 3 g |
| Soya saponins | 0.05 g |
| Madecassoside | 0.05 g |
| Parsol MCX | 7 g |
| Benzophenone 3 | 1 g |
| Shea butter | 1 g |
| Perfumed cream excipient | qsp 100 g |

This cream is to be applied as from late afternoon and makes it possible to repair wrinkles from inside and to protect the skin from the last rays of sunshine.

What is claimed is:

1. A skin care composition comprising an effective amount for increasing the amount of collagen IV in the dermo-epidermal junction of skin areas in need thereof of at least one soya plant saponin component selected from the group consisting of a soya plant triterpenic saponin, a soya plant triterpenic sapogenol, and a soya plant extract containing at least one of said soya plant triterpenic saponin and of said soya plant triterpenic sapogenol, with at least one ecdysteroid component selected from the group consisting of β-ecdysone and acylated β-ecdysone, ecdysterone, wherein said at least one soya plant saponin component is extracted from a soya plant selected from the group consisting of *Glycine max, Phaseolus vulgaris, Phaseolus aureus, Phaseolus lunatus, Vicia faba, Lens culinaris, Cicer arietum, Vigna angularis, Vigna mungo, Oxytropis ochrocephala, Oxytropis glabra, Pisum sativum, Sophora favescens, Asparalus membranaceus, Crotalaria albida, Arachis hypogea, Galega officinalis, Wistaria brachybotrys*, and *Trifolium repens*, wherein the combination of the soya plant saponin component and the ecdysteroid are employed in a synergistic effective amount.

2. The composition of claim 1, wherein the weight ratio of said saponin component to said ecdysteroid component is from 1:10 to 10:1.

3. The composition of claim 1, wherein the weight ratio of said saponin component to said ecdysteroid component is about 1:1.

4. A skin care composition comprising an effective amount for increasing the amount of collagen IV in the dermo-epidermal junction of skin areas in need thereof, of at least one soya plant saponin component selected from the group consisting of a soya plant triterpenic saponin, a soya plant triterpenic sapogenol, and a soya plant extract containing at least one of said soya plant triterpenic saponin and of said soya plant triterpenic sapogenol, with at least one ecdysteroid component selected from the group consisting of an β-ecdysone and acetylated β-ecdysone, wherein said at least soya plant saponin component is extracted from a soya plant selected from the group consisting of *Glycine max, Phaseolus vulgaris, Phaseolus aureus, Phaseolus lunatus, Vicia faba, Lens culinaris, Cicer arietum, Vigna angularis, Vigna mungo, Oxytropis ochrocephala, Oxytropis glabra, Pisum sativum, Sophora favescens, Asparalus membranaceus, Crotalaria albida, Arachis hypogea, Galega officinalis, Wistaria brachybotyrs*, and *Trifolium repens*, and wherein said composition is a cream comprising:

| | |
|---|---|
| Retinol | 4000 IU |
| Type B soya saponins | 0.01 g |
| Glycerol | 3 g |
| Extract of Commiphora mukkul | 0.01 g |
| Excipient | qsp 100 g. |

5. A skin care composition comprising an effective amount for increasing the amount of collagen IV in the dermo-epidermal junction of skin areas in need thereof, of at least one soya plant saponin component selected from the group consisting of a soya plant triterpenic saponin, a soya plant triterpenin sapogenol, and a soya plant extract containing at least one of said soya plant triterpenic saponin and of said soya plant triterpenic sapogenol, with at least one ecdysteroid component selected from the group consisting of an ecdysteroid, an aceylated ecdysteroid, β-ecdysone, ecdysterone, acetylated β-ecdysone and acylated ecdysterone, wherein said at least soya plant saponin component is extracted from a soya plant selected from the group consisting of *Glycine max, Phaseolus vulgaris, Phaseolus aureus, Phaseolus lunatus, Vicia faba, Lens culinaris, Cicer arietum, Vigna angularis, Vigna mungo, Oxytropis ochrocephala, Oxytropis glabra, Pisum sativum, Sophora favescens, Asparalus membranaceus, Crotalaria albida, Arachis hypogea, Galega officinalis, Wistaria brachybotyrs*, and *Trifolium repens*, and wherein said composition is a cream comprising:

| | |
|---|---|
| Retinol | 2000 IU |
| Retinol palmitate | 0.01 g |
| Ascorbyl palmitate | 0.1 g |
| Wheat proteins | 3 g |
| Soya saponins | 0.05 g |
| Madecassoside | 0.05 g |
| Ultraviolet filter | 7 g |
| Benzophenone 3 | 1 g |
| Shea butter | 1 g |
| Excipient | qsp 100 g. |

6. A pharmaceutical composition comprising a pharmaceutically effective amount for increasing the amount of collagen IV in the dermo-epidermal junction of skin areas in need thereof of
   (a) at least one soya plant saponin component selected from the group consisting of a soya plant triterpenic saponin, a soya plant triterpenic sapogenol, and a soya plant extract containing at least one of said soya plant triterpenic saponin and of said soya plant triterpenic sapogenol; and
   (b) at least one ecdysteroid component selected from the group consisting of β-ecdysone and acylated β-ecdysone,
   (c) wherein said at least one soya plant saponin component is extracted from a soya plant selected from the group consisting of *Glycine max, Phaseolus vulgaris, Phaseolus aureus, Phaseolus lunatus, Vicia faba, Lens culinaris, Cicer arietum, Vigna angularis, Vigna mungo, Oxytropis ochrocephala, Oxytropis glabra, Pisum sativum, Sophora favescens, Asparalus membranaceus, Crotalaria albida, Arachis hypogea, Galega officinalis, Wistaria brachybotrys*, and *Trifolium repens*, wherein the combination of the soya plant saponin component and the ecdysteroid are employed in a synergistic effective amount.

7. The composition of claim 6, wherein the weight ratio of said saponin component to said ecdysteroid component is from 1:10 to 10:1.

8. The composition of claim 6, wherein the weight ratio of said saponin component and to ecdysteroid component is about 1:1.

9. A method for skin care providing an anti-wrinkle skin effect, comprising topical application on skin areas in need thereof of an anti-wrinkle effective amount for increasing the amount of collagen IV in the dermo-epidermal junction of at least one soya plant saponin component selected from the group consisting of a soya plant triterpenic saponin, a soya plant triterpenic sapogenol, and a soya plant extract containing at least one of said soya plant triterpenic saponin and of said soya plant triterpenic sapogenol wherein said at least one soya plant saponin component is extracted from a soya plant selected from the group consisting of *Glycine max, Phaseolus vulgaris, Phaseolus aureus, Phaseolus lunatus, Vicia faba, Lens culinaris, Cicer arietum, Vigna angularis, Vigna mungo, Oxytropis ochrocephala, Oxytropis glabra, Pisum sativum, Sophora favescens, Asparalus membranaceus, Crotalaria albida, Arachis hypogea, Galega officinalis, Wistaria brachybotrys*, and *Trifolium repens*, and wherein said soya plant saponin component is applied topically with ecdysteroid component selected from the group consisting of β-ecdysone and acylated β-ecdysone, wherein the combination of the soya plant saponin component and the ecdysteroid are employed in a synergistic effective amount.

10. The method of claim 9, wherein the weight ratio of the saponin component to the ecdysteroid component ranges from 1:10 and 10:1.

11. The method of claim 9, wherein the weight ratio of said saponin component to said ecdysteroid component is about 1:1.

12. A method of pharmaceutical treatment for improving the functional interface between the denims and the epidermis, comprising a topical application on skin areas in need thereof of at least one pharmaceutically acceptable soya plant saponin component selected from the group consisting of a soya plant triterpenic saponin, a soya plant triterpenic sapogenol, and a soya plant extract containing at least one of said soya plant triterpenic saponin and of said soya plant triterpenic sapogenol in a pharmaceutically effective amount for increasing the amount of collagen IV in the dermo-epidermal junction, wherein said at least one soya plant saponin component is extracted from a soya plant enriched in said triterpenic component selected from the group consisting of *Glycine max, Phaseolus vulgaris, Phaseolus aureus, Phaseolus lunatus, Vicia faba, Lens culinaris, Cicer arietum, Vigna angularis, Vigna mungo, Oxytropis ochrocephala, Oxytropis glabra, Pisum sativum, Sophora favescens, Asparalus membranaceus, Crotalaria albida, Arachis hypogea, Galega officinalis, Wistaria brachybotrys*, and *Trifolium repens*, and wherein said soya plant saponin component is topically applied with at least one ecdysteroid component selected from the group consisting of β-ecdysone and acylated β-ecdysone, wherein the combination of the soya plant saponin component and the ecdysteroid are employed in a synergistic effective amount.

13. The method of claim 12, wherein said ecdysteroid component is selected from the group consisting of β-ecdysone, ecdysterone, acetylated β-ecdysone, and acetylated ecdysterone.

14. The method of claim 12, wherein the ratio of saponin component to the ecdysteroid component ranges from of between 1:10 and 10:1.

15. The method of claim 12, wherein the ratio of said saponin component to said ecdysteroid component is about 1:1.

16. A method for skin care for improving the functional interface between the dermis and the epidermis, comprising a topical application on skin areas in need thereof, of at least one soya plant saponin component selected from the group consisting of a soya plant triterpenic saponin, a soya plant triterpenic sapogenol, and a soya plant extract containing at least one of said soya plant triterpenic saponin and of said soya plant triterpenic sapogenol, in an effective amount for increasing the amount of collagen IV in the dermo-epidermal junction, wherein said at least soya plant saponin component is extracted from a soya plant selected from the group consisting of *Glycine max, Phaseolus vulgaris, Phaseolus aureus, Phaseolus lunatus, Vicia faba, Lens culinaris, Cicer arietum, Vigna angularis, Vigna mungo, Oxytropis ochrocephala, Oxytropis glabra, Pisum sativum, Sophora favescens, Asparalus membranaceus, Crotalaria albida, Arachis hypogea, Galega officinalis, Wistaria brachybotyrs*, and *Trifolium repens*, and wherein the topical application on the skin areas in need thereof includes applying a cream comprising:

| | |
|---|---|
| Retinol | 4000 IU |
| Type B soya saponins | 0.01 g |
| Glycerol | 3 g |
| Extract of Commiphora mukkul | 0.01 g |
| Excipient | qsp 100 g. |

17. A method for skin care for improving the functional interface between the dermis and the epidermis, comprising a topical application on skin areas in need thereof, of at least one soya plant saponin component selected from the group consisting of a soya plant triterpenic saponin, a soya plant triterpenic sapogenol, and a soya plant extract containing at least one of said soya plant triterpenic saponin and of said soya plant triterpenic sapogenol, in an effective amount for increasing the amount of collagen IV in the dermo-epidermal junction, wherein said at least soya plant saponin component is extracted from a soya plant selected from the group consisting of *Glycine max, Phaseolus vulgaris, Phaseolus aureus, Phaseolus lunatus, Vicia faba, Lens culinaris, Cicer arietum, Vigna angularis, Vigna mungo, Oxytropis ochrocephala, Oxytropis glabra, Pisum sativum, Sophora favescens, Asparalus membranaceus, Crotalaria albida, Arachis hypogea, Galega officinalis, Wistaria brachybotyrs*, and *Trifolium repens*, and wherein the topical application on skin areas in need thereof includes applying a cream comprising,

| | |
|---|---|
| Retinol | 2000 IU |
| Retinol palmitate | 0.01 g |
| Ascorbyl palmitate | 0.1 g |
| Wheat proteins | 3 g |
| Soya saponins | 0.05 g |
| Madecassoside | 0.05 g |
| Ultraviolet filter | 7 g |
| Benzophenone 3 | 1 g |
| Shea butter | 1 g |
| Excipient | qsp 100 g. |

* * * * *